US008282671B2

(12) United States Patent
Connor (10) Patent No.: US 8,282,671 B2
(45) Date of Patent: Oct. 9, 2012

(54) SMART DEVICE FOR NON-INVASIVE SKELETAL ADJUSTMENT (75) Inventor: Robert A. Connor, Minneapolis, MN (US)

(73) Assignee: Orthonex, Forest Lake, MN (US)

(*) Notice: Subject to any disclaimer, the term of this patent is extended or adjusted under 35 U.S.C. 154(b) by 127 days.

(21) Appl. No.: 12/925,567

(22) Filed: Oct. 25, 2010

(65) Prior Publication Data
US 2012/0101527 A1 Apr. 26, 2012

(51) Int. Cl.
A61B 17/70 (2006.01)
(52) U.S. Cl. ........................ 606/246; 606/263
(58) Field of Classification Search .......... 606/276–279, 606/25–265; 600/309, 594, 12, 424, 587
See application file for complete search history.

(56) References Cited

U.S. PATENT DOCUMENTS

| 5,092,866 | A | 3/1992 | Breard et al. |
| 5,501,684 | A | 3/1996 | Schlapfer et al. |
| 5,626,579 | A | 5/1997 | Muschler et al. |
| 5,672,175 | A | 9/1997 | Martin |
| 5,704,939 | A | 1/1998 | Justin |
| 6,033,412 | A | 3/2000 | Losken et al. |
| 6,106,525 | A | 8/2000 | Sachse |
| 6,245,075 | B1 | 6/2001 | Betz et al. |
| 6,375,682 | B1 | 4/2002 | Fleischmann et al. |
| 6,417,750 | B1 | 7/2002 | Sohn |
| 6,551,320 | B2* | 4/2003 | Lieberman .................... 606/263 |
| 6,673,079 | B1 | 1/2004 | Kane |
| 6,682,533 | B1 | 1/2004 | Dinsdale et al. |
| 6,716,216 | B1 | 4/2004 | Boucher et al. |
| 6,835,207 | B2 | 12/2004 | Zacouto et al. |
| 6,849,076 | B2 | 2/2005 | Blunn et al. |
| 6,918,910 | B2 | 7/2005 | Smith et al. |
| 7,066,957 | B2 | 6/2006 | Graf |
| 7,135,022 | B2 | 11/2006 | Kosashvili et al. |
| 7,291,150 | B2 | 11/2007 | Graf |
| 7,481,841 | B2 | 1/2009 | Hazebrouck et al. |
| 7,542,791 | B2* | 6/2009 | Mire et al. .................... 600/407 |
| 7,559,951 | B2 | 7/2009 | DiSilvestro et al. |
| 7,588,589 | B2* | 9/2009 | Falahee ........................ 606/247 |
| 7,611,526 | B2 | 11/2009 | Carl et al. |
| 7,632,292 | B2* | 12/2009 | Sengupta et al. ............. 606/257 |
| 7,658,753 | B2 | 2/2010 | Carl et al. |
| 7,708,737 | B2 | 5/2010 | Kraft et al. |
| 7,708,765 | B2* | 5/2010 | Carl et al. .................... 606/279 |
| 7,708,779 | B2 | 5/2010 | Edie et al. |
| 7,722,649 | B2* | 5/2010 | Biedermann et al. ......... 606/257 |
| 7,722,675 | B2 | 5/2010 | Ralph et al. |
| 7,736,305 | B2 | 6/2010 | DiPoto |
| 7,763,053 | B2 | 7/2010 | Gordon |
| 7,766,941 | B2 | 8/2010 | Paul |
| 7,799,060 | B2* | 9/2010 | Lange et al. .................. 606/257 |
| 2002/0151978 | A1 | 10/2002 | Zacouto et al. |
| 2004/0152972 | A1 | 8/2004 | Hunter |
| 2005/0055025 | A1 | 3/2005 | Zacouto et al. |

(Continued)

Primary Examiner — Pedro Philogene (57) ABSTRACT

This invention is an implantable device and system that allows post-operative, non-invasive adjustment of members of the skeletal system. It includes extension-resisting members and a compression-resisting member that connect members of the skeletal system. Post-operative, non-invasive adjustment of the tensions, lengths, widths, and/or torsions of the extension-resisting members changes the relative movement, position, or both movement and position of members of the skeletal system. The compression-resisting member may act as a fulcrum. This invention can help to pioneer the evolution of "smart" orthopedic devices that adjust skeletal biodynamics to address changing clinical needs and changes in patient activity over time. Some promising applications include: dynamic stabilization of the spine; correction of scoliosis; and bone elongation.

19 Claims, 9 Drawing Sheets

U.S. PATENT DOCUMENTS

| | | |
|---|---|---|
| 2005/0234555 A1 | 10/2005 | Sutton et al. |
| 2006/0004447 A1 | 1/2006 | Mastrorio et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036324 A1 | 2/2006 | Sachs et al. |
| 2007/0173855 A1 | 7/2007 | Winn et al. |
| 2007/0232958 A1 | 10/2007 | Donofrio et al. |
| 2007/0233065 A1 | 10/2007 | Donofrio et al. |
| 2007/0233098 A1 | 10/2007 | Mastrorio et al. |
| 2007/0233254 A1 | 10/2007 | Grotz et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276369 A1 | 11/2007 | Allard et al. |
| 2008/0021466 A1 | 1/2008 | Shadduck et al. |
| 2008/0154307 A1 | 6/2008 | Colleran et al. |
| 2008/0161933 A1 | 7/2008 | Grotz et al. |
| 2009/0012565 A1 | 1/2009 | Sachs et al. |
| 2009/0076597 A1 | 3/2009 | Dahlgren et al. |
| 2009/0093820 A1 | 4/2009 | Trieu et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0234388 A1 | 9/2009 | Patterson et al. |
| 2009/0234456 A1 | 9/2009 | Nycz |
| 2010/0049204 A1 | 2/2010 | Soubeiran |
| 2010/0070033 A1 | 3/2010 | Doty |
| 2010/0094302 A1 | 4/2010 | Pool et al. |
| 2010/0094303 A1 | 4/2010 | Chang et al. |
| 2010/0094304 A1 | 4/2010 | Pool |
| 2010/0094305 A1 | 4/2010 | Chang |
| 2010/0094306 A1 | 4/2010 | Chang |
| 2010/0100133 A1 | 4/2010 | Carl et al. |
| 2010/0114103 A1 | 5/2010 | Harrison et al. |
| 2010/0191288 A1 | 7/2010 | Carl et al. |
| 2010/0198261 A1 | 8/2010 | Trieu et al. |
| 2010/0211106 A1 * | 8/2010 | Bowden et al. ............... 606/260 |
| 2010/0262160 A1 | 10/2010 | Boyden et al. |
| 2010/0262239 A1 | 10/2010 | Boyden et al. |
| 2010/0262247 A1 | 10/2010 | Arnin |

* cited by examiner

SMART DEVICE FOR NON-INVASIVE SKELETAL ADJUSTMENT

CROSS-REFERENCE TO RELATED APPLICATIONS

This patent application claims the priority benefits of: U.S. patent application Ser. No. 12/460,261 entitled "Device for Dynamic Stabilization of the Spine" filed on Jul. 16, 2009 by Robert A. Connor; and U.S. patent application Ser. No. 12/322,837 entitled "Dynamic Stabilization Device with Tilting Rigid Segments and Non-Central Tensile Members" filed on Feb. 7, 2009 by Robert A. Connor.

FEDERALLY SPONSORED RESEARCH

Not Applicable

SEQUENCE LISTING OR PROGRAM

Not Applicable

FIELD OF INVENTION

This invention relates to devices for adjusting skeletal members.

Unmet Clinical Need and Review of the Prior Art

There are important clinical applications for an implantable device that would allow post-operative, non-invasive adjustment of the relative movement and positions of members of the skeletal system. Three such applications are: dynamic stabilization of the spine; correction of spinal deformity such as scoliosis; and bone elongation. Although progress has been made in orthopedic devices and methods in the prior art, there remains an unmet clinical need for better treatment options for these applications. In this section, we discuss this need and note the limitations of the prior art in meeting this need. In the section following this, we will discuss how the invention disclosed herein addresses these limitations and meets this clinical need.

Chronic lower back pain is a very common, significant, and costly health problem in the United States and the entire world. It is estimated that more than ten million people in the U.S. suffer from chronic back pain at any given time, that the annual prevalence of lower back pain is in the range of 15-45% of the population, and that thoracic and lumbar spinal disorders affect nearly three-quarters of the U.S. population some time during their lives. Chronic back pain can be debilitating, interfering with one's ability to work and enjoy recreational activities. It is the most common activity-limiting condition affecting people under the age of 45.

The leading cause of chronic lower back pain is degeneration of the semi-flexible discs between spinal vertebrae. There are non-invasive approaches to address chronic back pain, but sometimes they are inadequate and more invasive methods are required. Historically, a common invasive method has been to fuse selected spinal vertebrae together in an effort to eliminate disc movement and stop the pain. More than 150,000 lumbar fusions are done each year to immobilize selected vertebrae. However, there are limitations associated with fusing vertebrae. Fusion-related limitations include: undesirable restriction of natural spine movement (restrictions on spinal flexion, extension, lateral bending, and torsion) in fused segments; greater stress and degeneration affecting spinal segments adjacent to fused segments (a phenomenon called "transition syndrome"); bone loss in the immobilized segments; failure to stop the pain in approximately 20-25% of fusion cases; irreversibility of the procedure; and the invasiveness, health risks, and relatively long recovery period associated with the surgery.

Due to the limitations associated with the complete immobilization of selected vertebrae in fusion, there has been an increasing trend toward alternative methods of addressing back pain that preserve some spinal mobility. "Dynamic Stabilization" is the term for methods that seek to maintain desirable spinal movement, but limit undesirable spinal movement. The ultimate form of dynamic stabilization would be to artificially recreate the natural biodynamics of a healthy spine. Since the original spine is not entirely replaced, the challenge is to recreate natural biodynamics in an integrated manner with those portions of the original spine which are working properly and remain in place. Due to the complexity of spinal biomechanics, this is not an easy goal.

With respect to limiting undesirable movement, dynamic stabilization seeks to: relieve the load and correct improper vertebral movement in areas where pain is caused by compression and improper vertebral movement; maintain proper rigidity, stabilization, and vertical support of the spinal column; avoid abnormal range of motion; and ensure the long-term durability of the spinal structure, including any implants.

With respect to allowing or enhancing desirable movement, dynamic stabilization seeks to allow normal biomechanical direction and range of motion including flexion (bending forward/anteriorly), extension (bending backward/posteriorly), lateral bending (right and left side bending), torsion (axial rotational movement), and limited longitudinal elongation or compression (so-called "shock absorber" functionality). In addition to the mobility and comfort advantages for patients, allowing normal motion can also help to avoid loss of bone density for diseased segments and more evenly distribute load across different portions of the spinal column to avoid creating stress-induced problems elsewhere. Allowing desirable spinal movement is particularly important for young patients.

Progress has been made toward developing methods of dynamic stabilization to provide the correct balance of allowing desirable movement and limiting undesirable movement. However, this remains a challenge. Current treatment options have limitations. Some methods undesirably restrict natural spine movement in one or more directions (flexion, extension, lateral bending, and torsion). Some methods immobilize a section of the spine causing greater stress, unnatural movement, and degeneration of adjacent portions of the spine (a phenomenon called "transition syndrome"). Some methods allow multi-directional movement without the ability to selectively control the degree or range of movement in different directions (flexion, extension, lateral bending, and torsion). They do not provide sufficient vertical support of the spinal column. Some methods and devices may be prone to mechanical or material failure due to repeated flexing of materials or components. Some methods are not adjustable to meet the specific needs and features of different patients. For example, they may not be adjustable after implantation to refine therapy or to accommodate patient growth. Accordingly, there is still a need for new approaches to dynamic stabilization that address these limitations and provide better treatment options for the millions of people who suffer from chronic back pain.

The prior art in this area includes implantable devices with adjustable-length rigid members (such as threaded rods or concentric hydraulic members) that connect two or more members of the skeletal system. Adjustment of the lengths of these rigid members can change the distance between members of the skeletal system. Such adjustment can be accomplished by rotation of threaded members, by pressurization of hydraulic members, or by other means. The prior art includes discussion of such adjustments being done in a post-operative and non-invasive manner. For example, external application of a rotating magnetic field can interact with an implanted magnetic member within the body to rotate that member. Rotation of that member can, in turn, rotate a threaded rod connecting two skeletal members, thereby changing the distance between these two skeletal members. Such prior art can be useful for gradual correction of scoliosis over time, for post-operative adjustment of spinal stabilization devices, and for bone elongation applications.

There are, however, limitations with implantable devices with adjustable-length rigid members that connect members of the skeletal system, even if they can be post-operatively and non-invasively adjusted. For example, due the rigid nature of the connecting members, such devices are useful for holding the connected skeletal members in a relatively static configuration, but such devices are less useful for adjusting or controlling the range of motion among skeletal members. They are not well suited for controlling dampened movement within a desired range of motion and providing increasing resistance as the boundaries of this range are approached.

In these respects, devices with adjustable-length rigid members are very useful for bone elongation applications in which the connected bones do not have to move relative to each other, but only fuse together. Such devices can also be useful for stabilization of the spine or for correction of scoliosis in cases wherein restriction of extension, flexion, tilting, bending, and/or torsion of the spine can be tolerated by the patent's activities and such restriction does not cause harm to the adjacent vertebrae. However, such devices are not ideal for dynamic stabilization of the spine or for correction of scoliosis if extension, flexion, tilting, bending, and/or torsion of the spine must be maintained within a desired range of motion. Thus, there remains an unmet clinical need for a device that can offer more precise management of the degree of dampening within a desired range of motion and a gradual increase in resistance as the boundaries of that desirable range are approached.

The prior art also includes implantable devices with adjustable-length members that resist both expansion and compression, but are laterally flexible. These members may be used to connect two or more members of the skeletal system. Extension of such members can increase the distance between the members of the skeletal system. Contraction of such members can decrease the distance between the members of the skeletal system. Such adjustments can be accomplished by rotation of threaded members, by pressurization of hydraulic components, or by other means.

There are, however, limitations with implantable devices with adjustable-length members that resist both expansion and compression, but are laterally flexible. Although they can provide more flexibility than devices with rigid adjustable-length connectors, they share some of the same limitations. They are useful for holding the connected skeletal members in a relatively static configuration, but are less useful for precise control of the range of motion of moving skeletal members relative to each other. They do not provide good control for dampened movement within a desired range of motion with increasing resistance as the boundaries of this range are approached. Devices with adjustable-length members that resist both expansion and compression, but are laterally flexible, also have limitations that devices with rigid members do not have. For example, a member that is strong enough to resist compression but flexible enough to bend can be prone to structural weakening and failure over time. As we will discuss, a device that has separate members to provide the extension-resisting and compression-resisting functions can reduce this problem because the separate members can be specifically designed to resist extension vs. resist compression, rather than trying to combine both functions into a single structural member.

The prior art also includes implantable devices featuring a rigid member (such as a rigid rod) on one side of the spinal column to which are also connected multiple extension-resisting members (such as cables) that are connected to members of the skeletal system. The lengths of the extension-resisting members may be adjusted so as to change the relative positions of the members of the skeletal system. Such devices may be useful for correcting scoliosis, especially when the lengths of the extension-resisting members can be post-operatively and remotely adjusted over time. However, such devices have limitations for dynamic stabilization of the spine. For example, such devices are asymmetric with respect to control of range of motion for the spinal column. They are useful for gradually bringing a curved spine into vertical alignment, but are less useful for creating a symmetric range of dampened motion for a spine that is in vertical alignment but which suffers from disc compression or range-of-motion problems. The rigidity of the rod member of such systems limits its applications for dynamic stabilization of the spine. Further, such devices are not well suited for bone elongation applications.

SUMMARY AND ADVANTAGES OF THIS INVENTION

This invention is an implantable device and system that allows post-operative, non-invasive adjustment of the movement, position, or both movement and position of members of the skeletal system relative to each other. This invention includes: two or more extension-resisting members that connect members of the skeletal system; and a compression-resisting member that also connects members of the skeletal system. Post-operative, non-invasive adjustment of the tension, length, width, and/or torsion of the extension-resisting members changes the relative movement, position, or both movement and position of members of the skeletal system to which these extension-resisting members are connected. The compression-resisting member may act as a fulcrum. These adjustments may be done by a human operator, automatically by a control unit, or by a combination of human and automatic means. These adjustments may include real-time responses to information from a sensor concerning skeletal movement and/or patient activity.

This invention may prove useful for many different orthopedic applications in which post-operative, non-invasive adjustment of skeletal system movement, flexibility, and range of motion is desirable. Some specific promising applications include: dynamic stabilization of the spine; correction of spinal deformities such as scoliosis, correction and healing of spinal injuries; and bone elongation. This invention offers several potential advantages over devices and systems in the prior art:

Compared to prior art featuring vertebral fusion, this invention: does not undesirably restrict natural spine movement (spinal flexion, extension, lateral bending, and torsion) in the affected segments; can cause less stress and degeneration of spinal segments adjacent to the affected segments (a phenomenon called "transition syndrome"); may cause less bone loss in the affected segments; and is a more reversible procedure than fusion.

Compared to prior art for dynamic stabilization of the spine with adjustable-length rigid members that connect members of the spinal column, this invention provides much better control and flexibility of movement within the desired range of motion and also offers gradually-increasing resistance as the boundaries of this range of motion are approached.

Compared to prior art for dynamic stabilization of the spine with adjustable-length members that resist both expansion and compression, but are laterally flexible, this invention provides much better control of allowable movement within the desired range of motion and gradual resistance as the boundaries of this range of motion are approached. The structural members of this invention are also less likely to weaken or fail with repeated movement because this invention has separate members for flexible resistance to expansion and for resistance to compression. Separating these functions into different members in this present invention allows structures and materials that are optimally targeted for these different functions, instead of trying to have a single member be both flexible and resist compression, as in the prior art.

Compared to prior art for correcting scoliosis with a rigid member on one side of the spinal column and multiple length-adjustable cables connected this rod to the spinal column, this present invention provides symmetric control of range of motion for dynamic stabilization of the spine. This present invention is also more universally applicable for other applications, such as bone elongation.

To summarize, this invention offers several potential advantages over the prior art in the field of orthopedics for applications including dynamic stabilization of the spine, correction of scoliosis, and bone elongation. Closing this section with an analogy, it may be noted that the first cardiac pacemakers did not adjust pacing in response to changes in patient activity. However, pacemakers have evolved since then and today's pacemakers are "smart" devices. These "smart" pacemakers offer sophisticated logic control units, sensors, and feedback algorithms that adjust pacing in real time based on changing patient clinical needs and activities. In some respects, today's orthopedic devices are where pacemakers were many years ago. Today's orthopedic devices are not "smart" devices that offer real-time adjustment of spinal biodynamics. However, the invention disclosed herein can help to pioneer the evolution of a new generation of "smart" orthopedic devices. These smart orthopedic devices will be able to adjust skeletal biodynamics to address changing clinical needs and changes in patient activity in real time.

BRIEF DESCRIPTION OF THE DRAWINGS

FIGS. 1 through 3 show a three-part sequence of a first example of the invention with: two extension-resisting members; and a compression-resisting member that is comprised of a connected longitudinal sequence of tiltable members. Members of the skeletal system are connected by the extension-resisting members and the compression-resisting member.

FIGS. 4 through 6 show a three-part sequence of a second example of the invention with: two extension-resisting members; and a compression-resisting member comprised of a gel-filled enclosure which can represent an artificial intervertebral disc.

FIGS. 7 and 8 show an example of how this invention may control rotation of skeletal members relative to each other.

DETAILED DESCRIPTION OF THE FIGURES

These figures show some alternative embodiments of this invention. However, these figures are only some of the potential embodiments and do not limit the full generalizability of the claims.

This invention is an implantable device that allows postoperative, non-invasive adjustment of the movement and/or positions of members of the skeletal system relative to each other. It may be used for dynamic stabilization of the spine, allowing dampened vertebral movement within a desired range of motion and preventing injurious movement outside that range. It may also be used for other orthopedic applications, such as scoliosis correction and bone elongation, which can benefit from the ability to remotely adjust the relative movement and/or positions of two or more members of the skeletal system.

Figure 1:
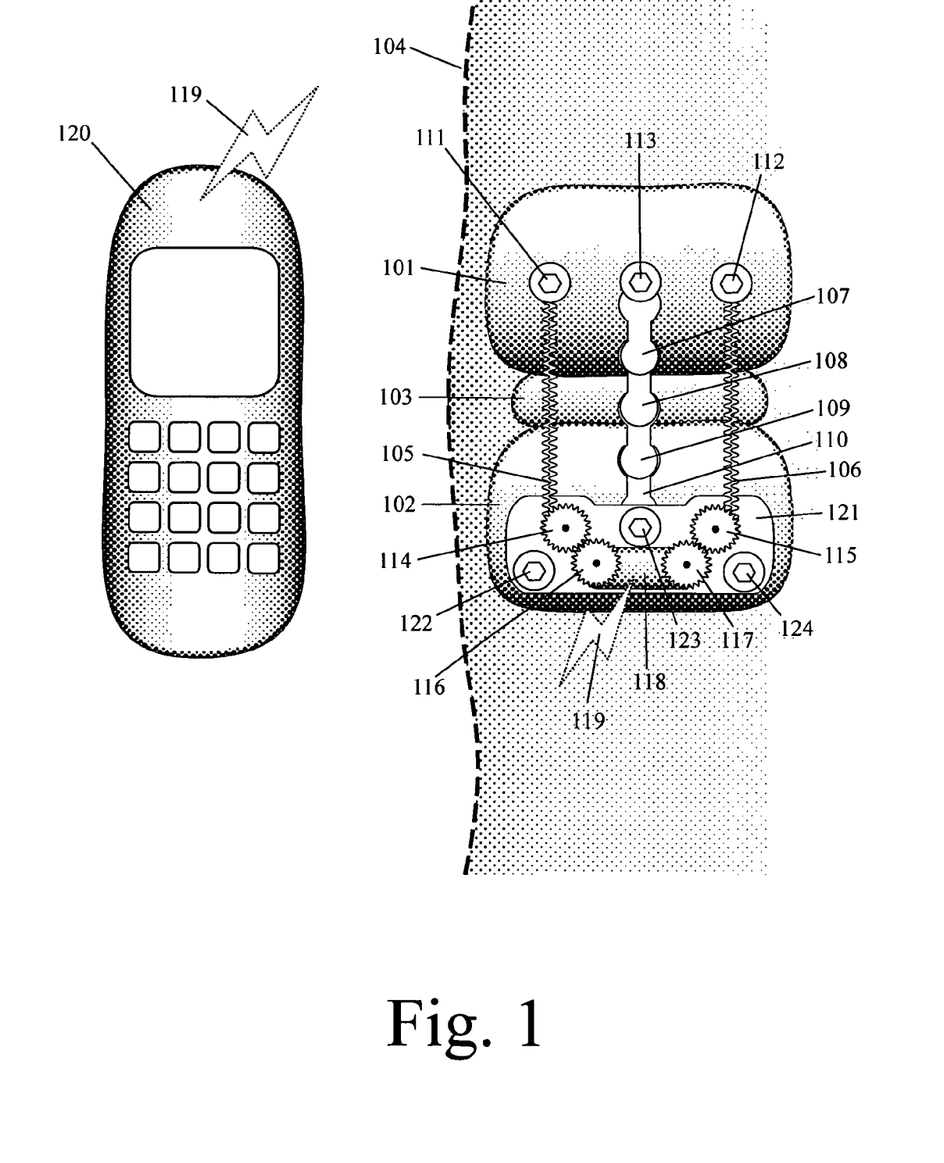
FIG. 1 shows a first part in this sequence in which skeletal members are aligned.
Figure 2:
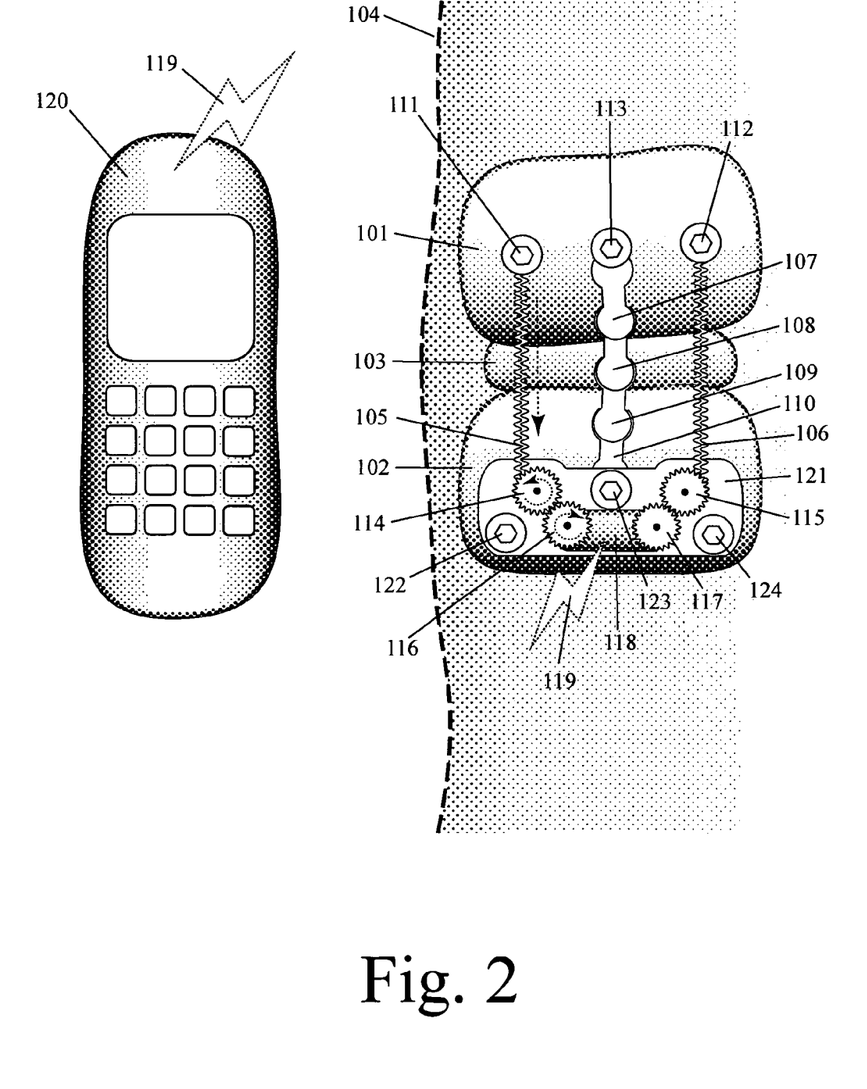
FIG. 2 shows a second part in this sequence in which changes in the extension-resisting members have tilted the upper skeletal member to the left.
Figure 3:
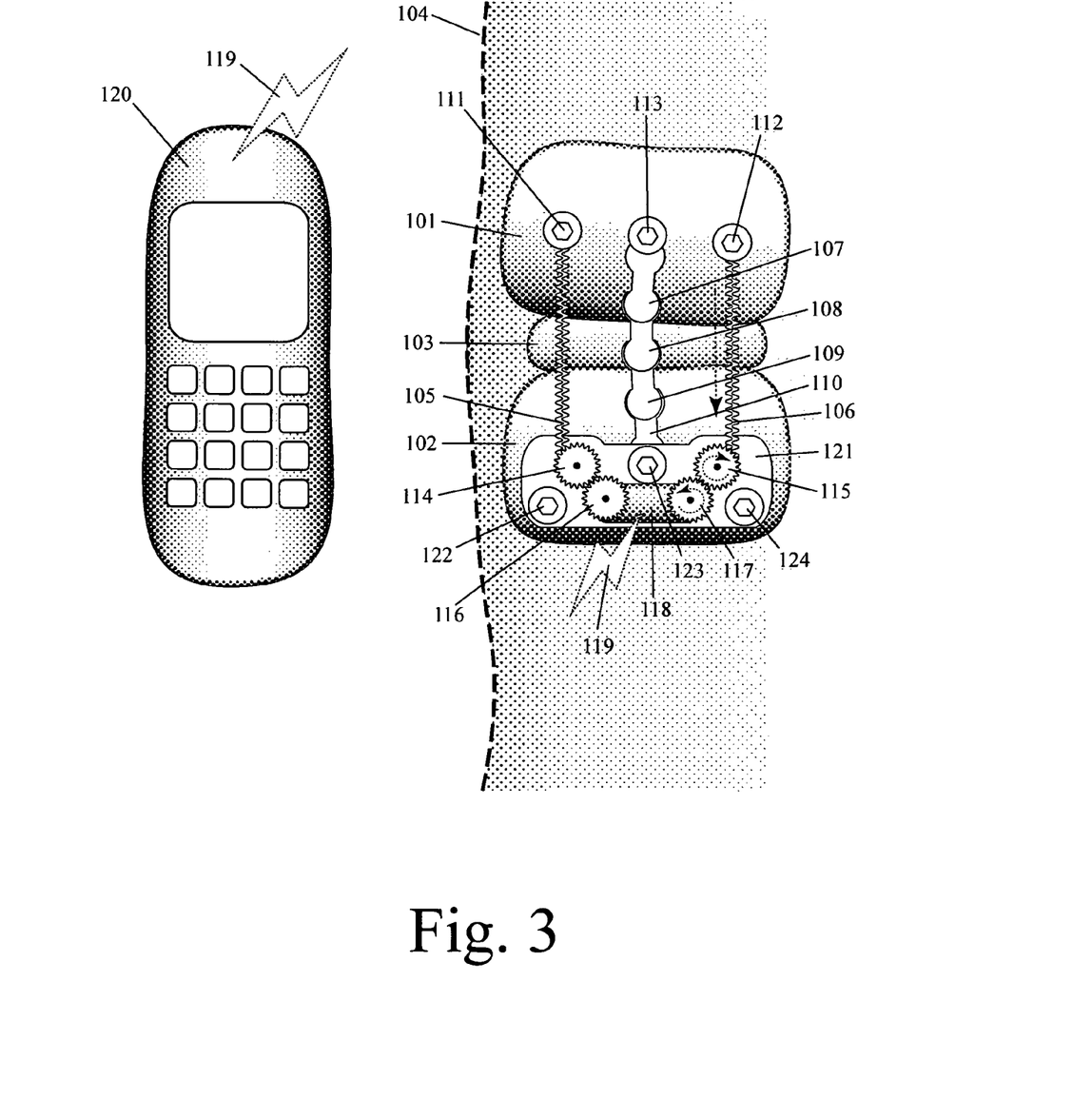
FIG. 3 shows a third part in this sequence in which changes in the extension-resisting members have tilted the upper skeletal member to the right.

The first example of this invention, shown in FIGS. 1 though 3, includes: two extension-resisting members, each of which connects two members of the skeletal system that can move relative to each other; a central compression-resisting member that also connects the two members of the skeletal system; an internal control unit with an actuator for changing the tensions and lengths or these extension-resisting members; and a remote control unit that is external to the body that can wirelessly control the internal control unit. In this example, changes in the tensions and lengths of the extension-resisting members change the movement and position of the members of the skeletal system relative to each other. In another example, changes in the width of an extension-resisting member may change the movement and position of members of the skeletal system. In this example, the compression-resisting member acts as a fulcrum with respect to movement of one or more members of the skeletal system caused by one or more changes in one or more extension-resisting members.

By way of overview, I note that FIGS. 1 through 3 show a three-part motion sequence for this first example of the invention. FIG. 1 shows this first example in a first configuration in which the members of the skeletal system are vertically aligned. FIG. 2 shows this first example in a second configuration in which changes in the relative tensions and lengths of the extension-resisting members have tilted the upper member of the skeletal system to the left. FIG. 3 shows this first example in a third configuration in which changes in the relative tensions and lengths of the extension-resisting members have tilted the upper member of the skeletal system to the right.

We now discuss FIGS. 1 through 3 in more detail. FIG. 1 shows the first configuration of the first example of this invention. FIG. 1 features rounded and shaded rectangles, 101 and 102, that are stylized depictions of two members of the skeletal system which can move relative to each other. Stylized depictions of skeletal members are shown, instead of actual members of the skeletal system with full anatomical detail, in order to more clearly show the features of this invention. Stylized depictions show the features of the invention with less clutter, for example, than would be the case if one were to show the anatomic complexities of skeletal members such as spinal vertebrae. Nonetheless, skeletal members 101 and 102 can be taken to represent stylized depictions of spinal vertebrae and rounded member 103 between them can taken to represent an intervertebral disc. In another example, skeletal members connected by this invention may be bones of the arm or leg which are directly connected by a joint instead of by a disc-like member.

Dashed line 104 and the accompanying shaded area to its right are stylized depictions of the outer surface and the interior of the body of a mammal. This line and shaded area highlight that the main body of the device is implanted within the body. However, the configuration of the device relative to the surface of the body as shown in FIG. 1 is only one possible configuration. In other examples and applications, the orientation and configuration of the device with respect to the body surface and with respect to the skeletal members may differ. In this example, the device is completely implanted within the body. In this example, post-operative adjustments can be made without penetration of the surface of the body by anything except electromagnetic signals. This may be called "non-invasive" or "minimally invasive" operation.

FIG. 1 shows two implanted extension-resisting members, 105 and 106, that are connected to skeletal members 101 and 102. FIG. 1 also shows a compression-resisting member that is comprised of a longitudinal sequence of four compression-resistant, but tiltable, segments 107, 108, 109 and 110 which connect skeletal members 101 and 102. In this example, the compression-resisting member is located between the two extension-resisting members, 105 and 106. In this manner, the compression-resisting member acts as a fulcrum for moving the skeletal members when one of the extension-resisting members is tightened or shortened relative to the other one. This process translates a change in the relative tensions or lengths of the two extension-resisting members, 105 and 106, into a change in the relative movement or positions of the two skeletal members, 101 and 102.

In this example, extension-resisting members 105 and 106 are extended by force from the relative movement of skeletal members 101 and 102, but they offer resistance to such extension. In this example, extension-resisting members 105 and 106 are uncovered springs. In another example, members 105 and 106 may be springs covered by flexible tubes. In other examples, extension-resisting members 105 and 106 may be selected from the group consisting of: one or more longitudinal members with cuts or slits; one or more extendable fibers; one or more extendable threads; one or more extendable cords; one or more extendable bands; one or more extendable wires; one or more extendable cables; one or more stretchable rods; and one or more extendable members filled with a gas, fluid, or gel. In other examples, the extension-resisting members may be structures created by a longitudinal parallel or longitudinal series combination of members selected from this group.

In this example, the compression-resisting member comprised of segments 107, 108, 109, and 110 is a longitudinal sequence of compression-resisting segments that are connected in such a way that they can be partially flexed, tilted, bent, rotated, or a combination of these movements, relative to each other, but that resist longitudinal compression when aligned in a straight configuration. In another example, this compression-resisting member may be a single compression-resisting longitudinal structure that can be flexed, tilted, bent, rotated, or a combination of these movements, but that resists longitudinal compression when aligned in a straight configuration. In another example, this compression-resisting member may be comprised of a "T-shaped" structure with a rigid longitudinal base and a tilting headpiece attached to this base. In another example, this compression-resisting member may be an artificial intervertebral disc that substitutes for body member 103, allowing flexion, extension, tilting, bending, and torsion of skeletal members 101 and 102 relative to each other, but resisting compression of the skeletal members 101 and 102 relative to each other.

As shown in the example in FIG. 1, extension-resisting member 105 is connected to skeletal member 101 by screw 111 and extension-resisting member 106 is connected to skeletal member 101 by screw 112. Top segment 107 of the compression-resisting member is connected to skeletal member 101 by screw 113. In other examples, the extension-resisting members and compression-resisting member may be connected to skeletal members by means other than screws, such as by means selected from the group consisting of: stapling; nails; adhesion; suturing; and hole drilling, threading, and tying; and connective tissue growth.

In this example, changes in the tensions and lengths of the extension-resisting members can cause changes in the relative motion and/or positions of skeletal members 101 and 102. In another example, changes in the widths of extension-resisting members may cause changes in the relative motion and/or positions of skeletal members. In this example, the bottom of extension-resisting member 105 is connected to gear 114 such that it winds around an inner portion of gear 114 as gear 114 rotates. In this manner, rotation of gear 114 changes the tension and length of extension-resisting member 105. Gear 114 is rotated by rotation of inter-meshed gear 116, which is driven by internal control unit 118. In a similar manner, extension-resisting member 106 is connected to gear 115 which is rotated by gear 117 which is driven by internal control unit 118. In this example, internal control unit 118 is attached to plate 121 which is attached to skeletal member 102 by means of screws 122, 123, and 124.

In this example, the tensions and lengths of the extension-resisting members are changed by rotational winding of their ends, as is done with guitar strings. In other examples, the tensions and lengths of the extension-resisting members may be made by changes in the internal pressure of hydraulic members or by rotation of threaded members. In other examples the torsion of the extension members may be changed by rotating them around their longitudinal axis at one end and holding them fixed at the other end. Changes in torsion can also change the relative position and movement of the skeletal members to which the extension-resisting members are connected.

There are many different types of control units in the prior art and the exact specification of internal control unit 118 is not central to this invention. Nonetheless, by way of a non-limiting example, we mention some components that may be included in internal control unit 118. Internal control unit 118 may include one or more: Micro Electro Mechanical Systems (MEMS) or other types of electromechanical actuators, electromagnetic circuits or other types of logic processing components, batteries, (electromagnetic) signal receptors, (electromagnetic) signal transmitters, and sensors.

In this example, the two extension-resisting members, 105 and 106, are directly connected to members of the skeletal system, 101 and 102. In other examples, the extension-resisting members may be indirectly connected to members of the skeletal system. In this example, one or more changes in an extension-resisting member (wherein a change is selected from the group consisting of a change in tension, a change in length, and a change in torsion) can cause one or more movements of the members of the skeletal system relative to each other (wherein a movement is selected from the group consisting of flexion, extension, tilting, bending, and torsion). In this example, causation can also occur in the other direction, with movement of the skeletal members causing changes in the extension-resisting members.

In different examples, changes in the extension-resisting members can be selected from the group consisting of a change in tension, a change in length, a change in width, and a change in torsion. In an example, changes in the tension of one or both extension-resisting members can cause one or more movements of two or more members of the skeletal system relative to each other (wherein a movement is selected from the group consisting of flexion, extension, tilting, bending, and torsion). In another example, changes in the length of one or both extension-resisting members can cause one or more movements of two or more members of the skeletal system relative to each other (wherein a movement is selected from the group consisting of flexion, extension, tilting, bending, and torsion). In another example, changes in the width of one or both extension-resisting members can cause one or more movements of two or more members of the skeletal system relative to each other (wherein a movement is selected from the group consisting of flexion, extension, tilting, bending, and torsion). In another example, changes in the torsion of one or both extension-resisting members cause one or more movements of two or more members of the skeletal system relative to each other (wherein a movement is selected from the group consisting of flexion, extension, tilting, bending, and torsion).

In this example, the compression-resisting member is connected directly to members of the skeletal system. In another example, the compression-resisting member may be connected indirectly to members of the skeletal system. In various examples, one or more changes in the extension-resisting members (wherein a change is selected from the group consisting of a change in tension, a change in length, a change in width, and a change in torsion) can cause one or more movements of the compression-resisting member (wherein a movement is selected from the group consisting of flexion, extension, tilting, bending, and torsion).

In this example, there are only two extension-resisting members. In other examples, there may be several extension-resisting members, possibly located on different sides of the sequence of skeletal members. In this example, there is one compression-resisting member. In other examples, there may be more than one compression-resisting member. In this example, the extension-resisting members and the compression-resisting member, although connected by plate 121, are primarily separate structures that are separately connected to skeletal members. In another example, the extension-resisting members and the compression-resisting member may be more fully integrated into a single structure. As an example of the latter, the device may be comprised of a longitudinal series of rigid tiltable segments, connected by ball-and-socket joints, wherein there are multiple extension-resisting members around the circumference of the rigid tiltable segments. In this latter case, the extension-resisting members may be inside channels within the tiltable segments or around the perimeter of the tiltable segments.

In this example, the top skeletal member is shown as moving and the bottom skeletal member does not move. In other examples, the bottom skeletal member may move or both of the skeletal members may move relative to each other. In this example, there is one set of connective members (comprising two extension-resisting members and one compression-resisting member) that connects one set of moving skeletal members. In other examples, there may be a sequence of multiple sets of connecting members (extension-resisting members and compression-resisting members) that connect a sequence of multiple sets of skeletal members. The latter may span a significant portion of the entire spinal column.

In this example, internal control unit 118 is controlled by means of an electromagnetic signal 119 that is emitted by remote control unit 120 that is located outside the body. In other examples, the remote control unit 120 may communicate with the internal control unit 118 by ultrasound, infrared light, or other means. In this example, a human operator uses remote control unit 120 to make post-operative and non-invasive changes, such as changes in tension and length, in extension-resisting members 105 and 106. In another example, changes in the extension-resisting members may be made automatically, without the need for human operation. The logical processing for this automated operation may occur in internal control unit 118, in external remote unit 120, or both. In another example, adjustments may be made by a combination of human operation and automated operation. In an example, post-operative changes in extension-resisting members 105 and 106 may be at least partially based on information from an implanted sensor.

FIG. 2 shows the same example of the invention that is shown in FIG. 1, except that now skeletal member 101 has been tilted to the left. Specifically, a human operator entered a command into remote control unit 120, which was transmitted via electromagnetic signal 119 to internal control unit 118, which rotated gear 116 clockwise, which rotated gear 114 counter-clockwise, which shortened the length and increased the tension of extension-resisting member 105, which pulled the left side of skeletal member 101 downwards (with compression-resisting sequence 107, 108, 109, and 110 acting as a fulcrum), causing skeletal member 101 to tilt to the left.

Since extension-resisting members 105 and 106 resist extension, but do not completely prevent it, skeletal members 101 and 102 can still move relative to each other. However, the angular and dampening specifics of the relative Range of Motion (ROM) of skeletal members 101 and 102 is changed by this adjustment. The capability of such post-operative non-invasive adjustment can be very useful for fine-tuning dynamic stabilization after implantation, reducing pain from compressed or bulging intervertebral discs, for tailoring dynamic stabilization at different times for different patient activities, for long-term correction of scoliosis, for gradual bone elongation, and for other orthopedic applications.

FIG. 3 shows the same example of the invention that is shown in FIG. 1, except that now skeletal member 101 has been tilted to the right. Specifically, a human operator entered a command into remote control unit 120, which was transmitted via electromagnetic signal 119 to internal control unit 118, which rotated gear 117 counter-clockwise, which rotated gear 115 clockwise, which shortened and increased the tension of extension-resisting member 106, which pulled the right side of skeletal member 101 downwards (with compression-resisting sequence 107, 108, 109, and 110 acting as a fulcrum), causing skeletal member 101 to tilt to the right.

In this example, shortening the length and increasing the tension of one of the extension-resisting members relative to the other extension-resisting member caused the skeletal members to tilt relative to each other. In another example, shortening the length and increasing the tension of both extension-resisting members equally would not cause the skeletal members to tilt, but would dampen and/or restrict the range of motion of the skeletal members relative to each other. In another example, elongating the length and decreasing the tension of both extension-resisting members equally would loosen and/or widen the range of motion of the skeletal members relative to each other.

This device offers the possibility for post-operative non-invasive adjustment of the relative position and movement of skeletal members. This adjustment may occur over a long period of time. For example, dysfunctional curvature of the spine (scoliosis) may be corrected by a series of gradual angular adjustments over weeks, months, or even years. As another example, bones may be gradually elongated by a series of gradual longitudinal adjustments over weeks, months, or even years. Alternatively, adjustments may be made over a relatively short time period. A device with automatic sensing and feedback capabilities may make adjustments in real time to facilitate certain patient activities or even avoid injuries.

By way of analogy, the first cardiac pacemakers paced at a constant pace that did not vary with changes in patient activity. However, today's pacemakers are sophisticated "smart" devices with complex sensing and control mechanisms that vary pacing based on multiple factors including changes in patient activity. With the capabilities provided by this present invention, orthopedic devices may make a similar evolution. Today's orthopedic devices, such as those for dynamic stabilization of the spine, do not offer real-time variation in range of motion based on changes in patient activity during the day. However, the range of motion for the spine that is desirable when a patient is sleeping may be quite different than range of motion that is desirable when a patient is golfing. The optimal amount of extending force applied to leg bones for elongation while a patient is sleeping may be quite different than the optimal force while a patient is jogging. This invention can help to pioneer a new generation of "smart" orthopedic devices with complex sensing and control mechanisms that vary range of motion with changes in patient activity. They may even be able to adjust spinal range of motion in real time to prevent injury.

Figure 4:
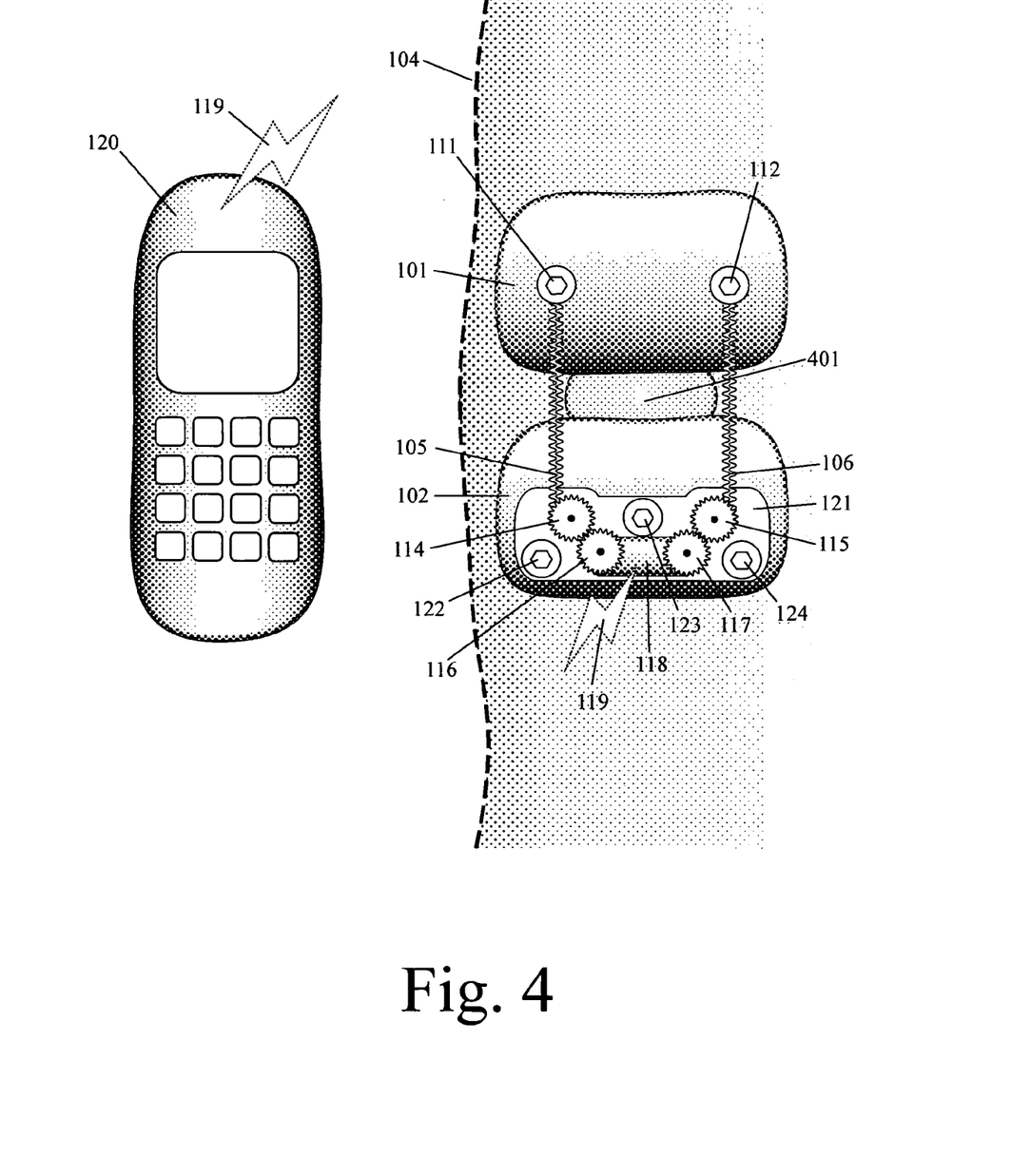
Figure 5:
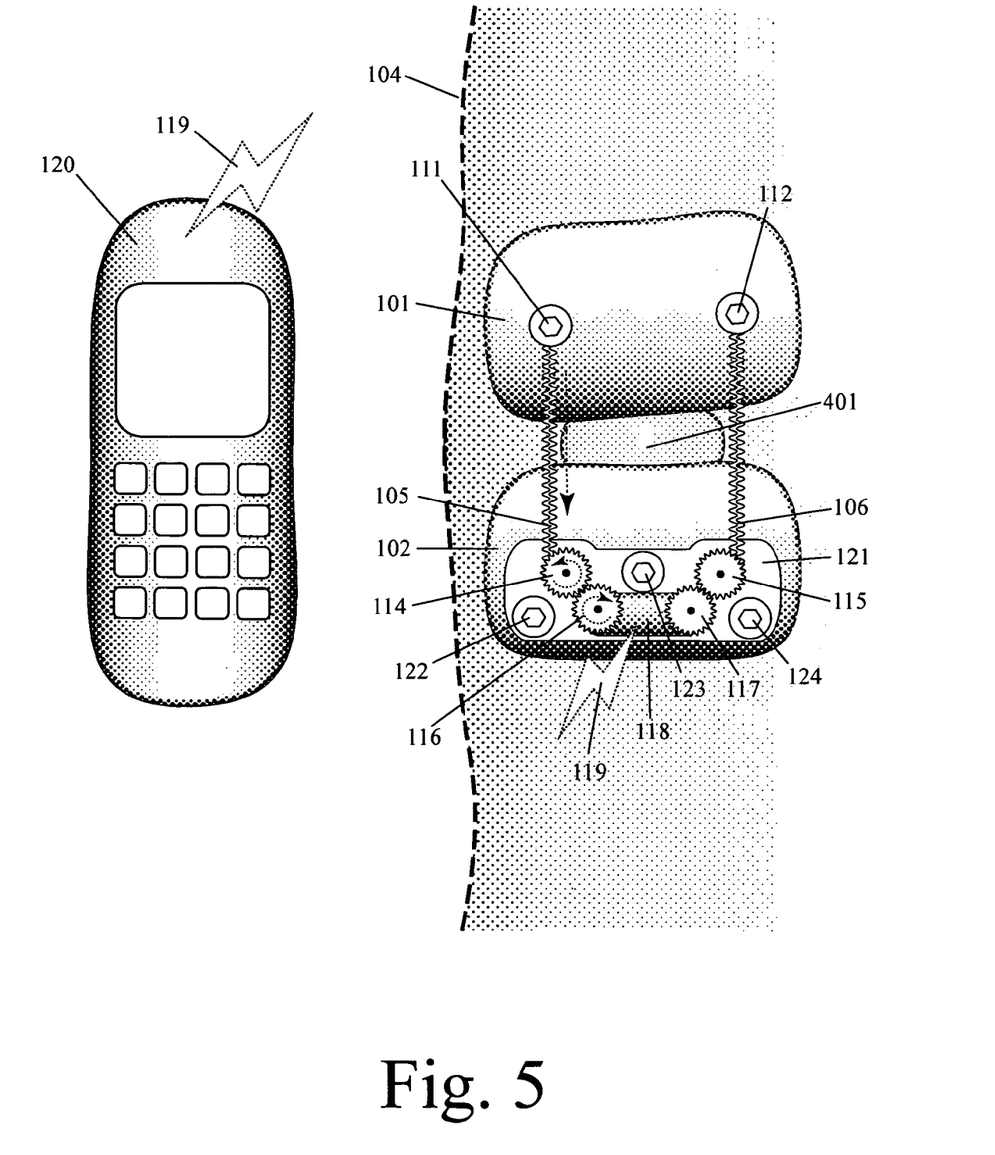
FIG. 5 shows a second part in this sequence in which changes in the extension-resisting members have tilted the upper skeletal member to the left.
Figure 6:
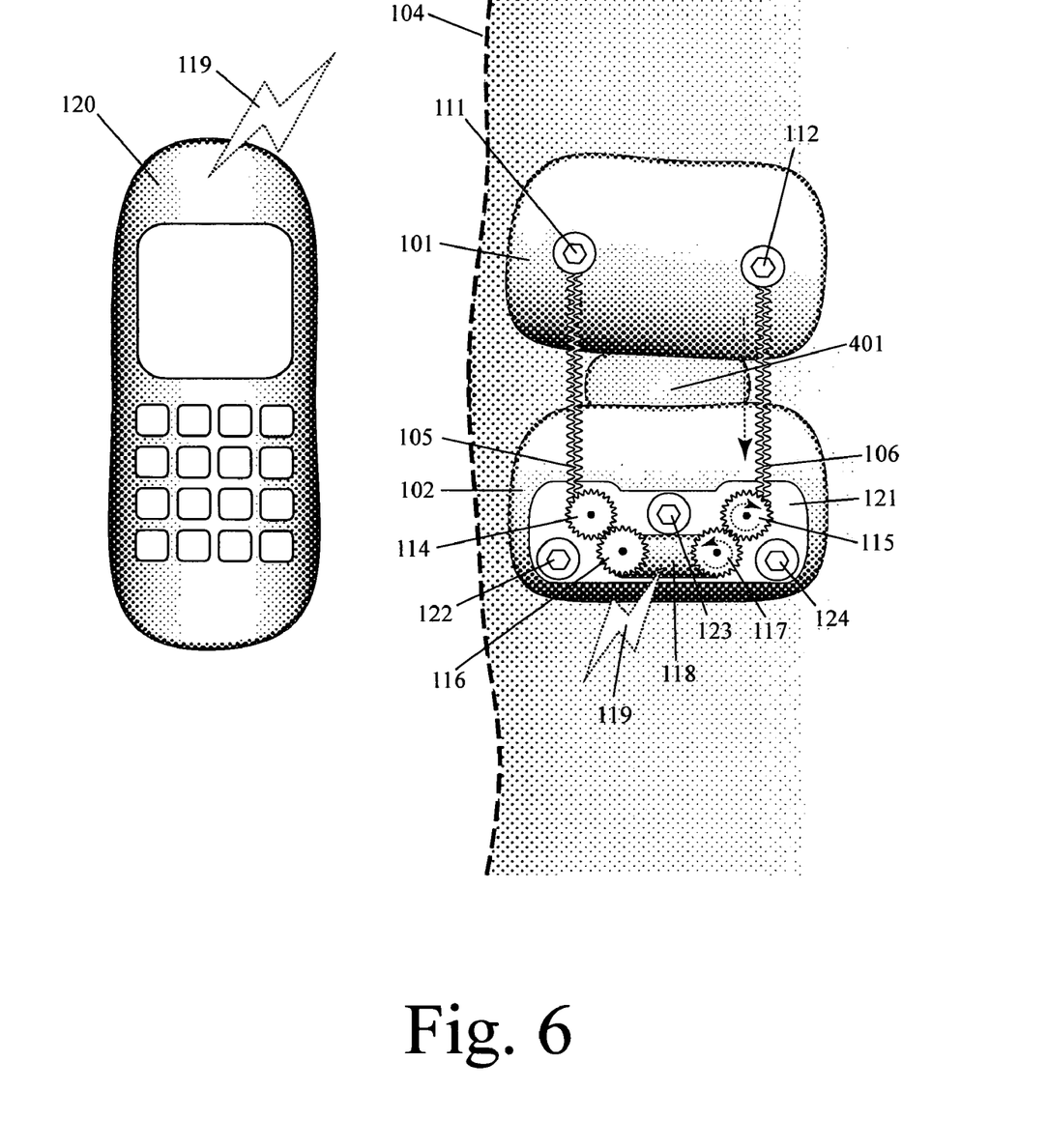
FIG. 6 shows a third part in this sequence in which changes in the extension-resisting members have tilted the upper skeletal member to the right.

FIGS. 4 through 6 show a three-part motion sequence of a second example of this invention. This second example is similar to the first example shown in FIGS. 1 through 3, except that now the compression-resisting member is an artificial disc 401 between skeletal members 101 and 102 instead of a longitudinal sequence of rigid segments. In FIG. 4, extension-resisting members 105 and 106 have equal lengths and tensions and skeletal members 101 and 102 are vertically aligned. Although the motion dynamics are somewhat different than those in the first example, there are some similarities. Similar to the longitudinal sequence of rigid segments in the first example, the artificial disc 401 in this second example resists compressive force from skeletal members 101 and 102 and acts a fulcrum in response to shortened length or increased tension in extension-resisting members 105 and 106.

In this example, there are only two extension-resisting members. In another example, if one wished to avoid forward tilting motion of 101 and 102 in response to shortened length or increased tension in extension-resisting members 105 and 106, then one could have a second pair of such extension-resisting members on the far-side of the skeletal members. This would result in a square defined by four extension-resisting members, with artificial disc 401 in the center of that square. In another example, one could have six or more parallel extension-resisting members, wherein their cross-sections are arranged in a circular manner around the longitudinal axis of the sequence of skeletal members. In other examples, there may also be extension-resisting members that are arranged in a diagonal, or other non-parallel, manner, such that shortening their length or increasing their tension exerts torque on skeletal members.

In this example, member 401, representing an intervertebral disc, is a free-form enclosure filled with a gel. In other examples, member 401 may be a free-form enclosure filled with a liquid or gas. In other examples, member 401 may be comprised of tilting, bending, sliding, rolling, or rotating components that combine to resist compression of skeletal members 101 and 102 relative to each other, but permit extension, flexion, tilting, bending, and torsion of skeletal members 101 and 102 relative to each other. Many different types of artificial discs are know in the prior art and the precise specification of member 401 is not central to this invention as long as it offers resistance to compression and allows some degree of extension, flexion, tilting, bending, and torsion.

FIG. 5 shows the same example of the invention as shown in FIG. 4, except that skeletal member 101 has now been tilted to the left. Specifically, a human operator entered a command into remote control unit 120, which was transmitted via electromagnetic signal 119 to internal control unit 118, which rotated gear 116 clockwise, which rotated gear 114 counter-clockwise, which shortened the length and increased the tension of extension-resisting member 105, which pulled the left side of skeletal member 101 downwards (with compression-resisting artificial disc 401 acting as a fulcrum), causing skeletal member 101 to tilt to the left.

FIG. 6 shows the same example of the invention as shown in FIG. 4, except that skeletal member 101 has now been tilted to the right. Specifically, a human operator entered a command into remote control unit 120, which was transmitted via electromagnetic signal 119 to internal control unit 118, which rotated gear 117 counter-clockwise, which rotated gear 115 clockwise, which shortened the length and increased the tension of extension-resisting member 106, which pulled the right side of skeletal member 101 downwards (with compression-resisting artificial disc 401 acting as a fulcrum), causing skeletal member 101 to tilt to the right.

Figure 7:
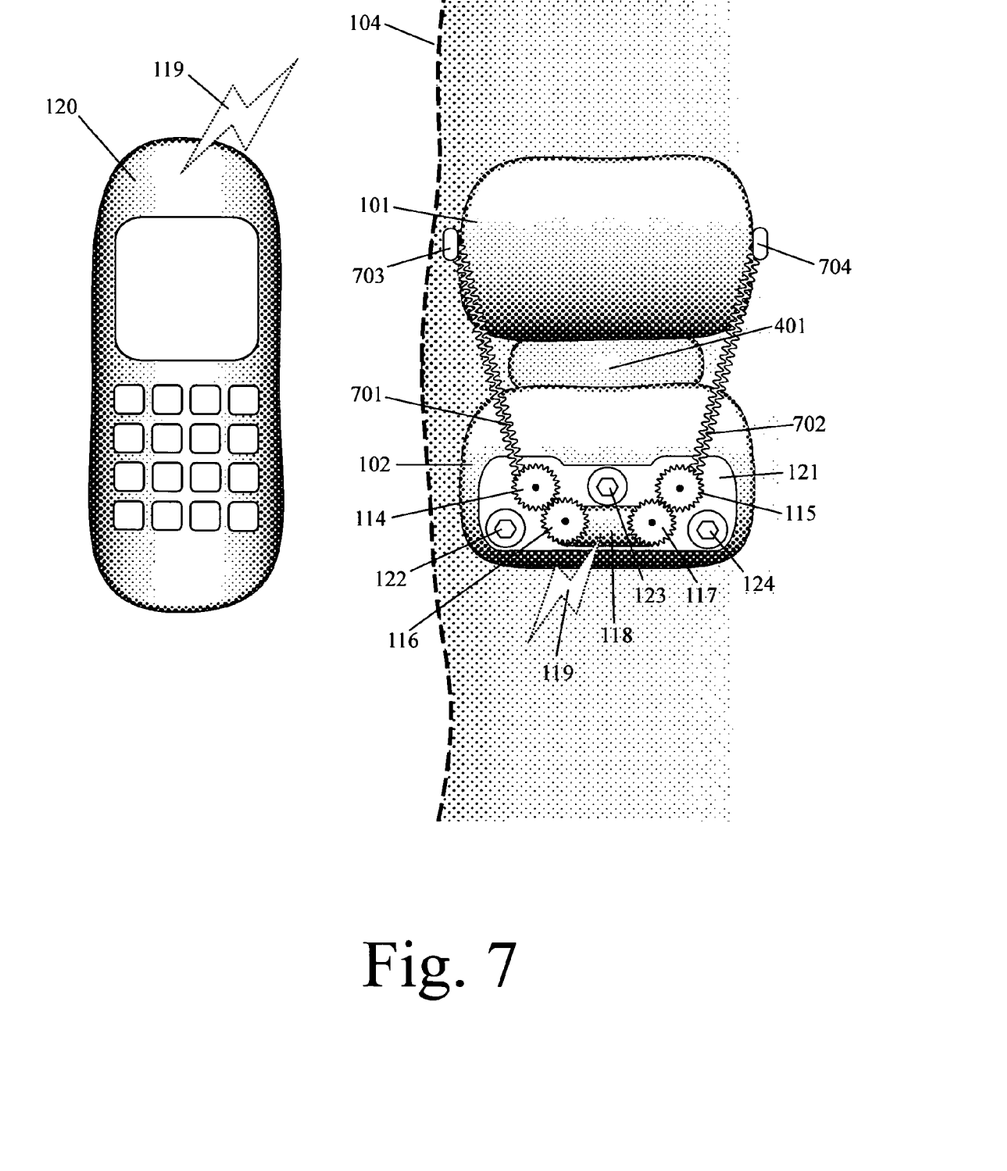
FIG. 7 shows an example wherein the tops of the extension-resisting members are attached to the sides of one skeletal member and the bottoms of these extension-resisting members are attached to the front of a second skeletal member.
Figure 8:
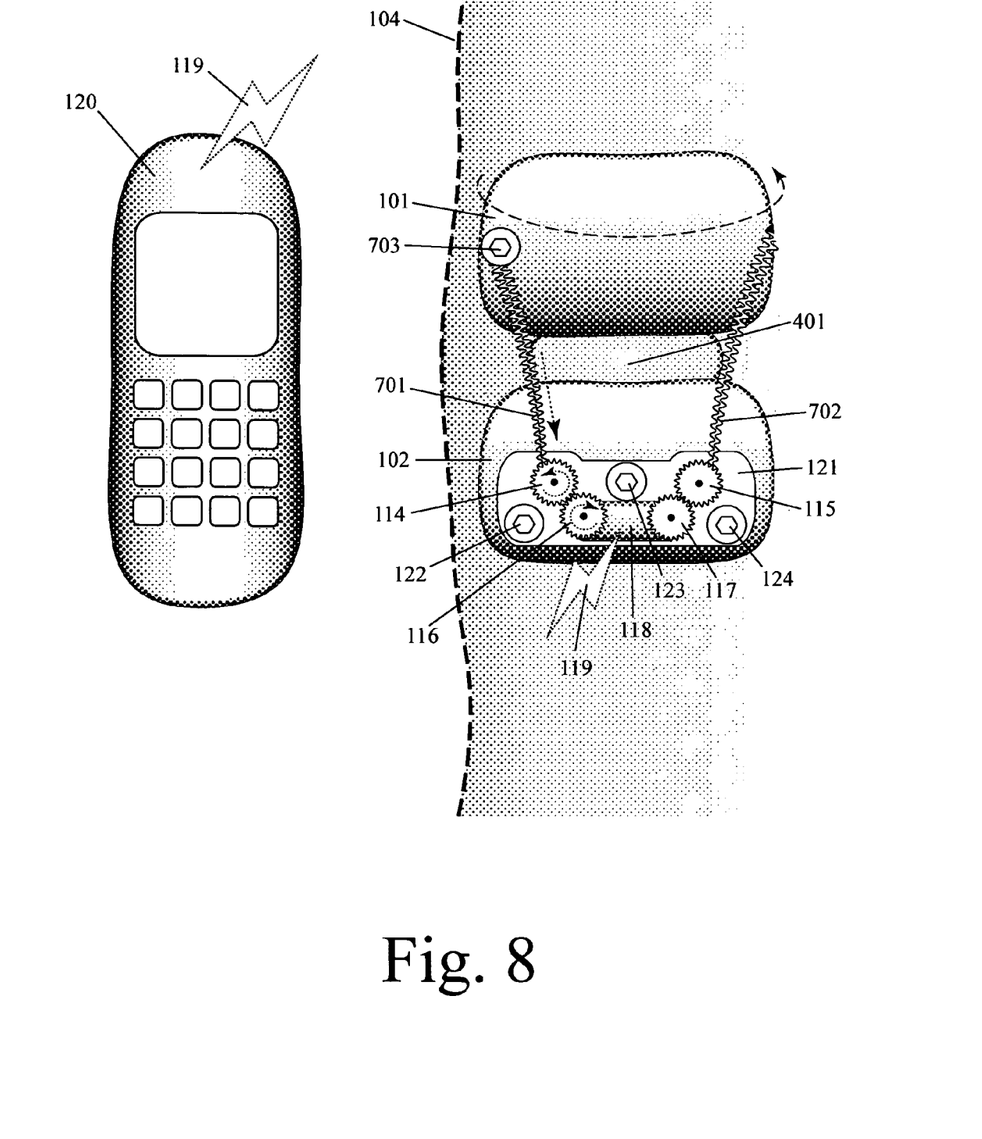
FIG. 8 shows how contraction of an extension-resisting member introduced in FIG. 7 causes the skeletal members to rotate relative to each other.

FIGS. 1 through 6 have demonstrated some examples of how this invention may be embodied to control tilting movement of members of the skeletal system relative to each other. This can represent flexion, extension, or bending of the spinal column. Now FIGS. 7 and 8 show an example of how this invention may be used to control rotation of members of the skeletal system relative to each other. This can represent torsion of the spinal column. In the example shown in FIG. 7, the tops of extension-resisting members 701 and 702 are attached to the sides of skeletal member 101, but the bottoms of extension-resisting members 701 and 702 are attached to the front of skeletal member 102. As a result of this diagonal or transverse configuration, shortening the length and increasing the tension of one of the extension-members relative to the other one causes skeletal member 101 to rotate relative to skeletal member 102. This can represent torsion of the spinal column.

FIG. 8 shows the same example of the invention that was shown in FIG. 7, except that now skeletal member 101 has been rotated clockwise relative to skeletal member 102. Specifically, a human operator entered a command into remote control unit 120, which was transmitted via electromagnetic signal 119 to internal control unit 118, which rotated gear 116 clockwise, which rotated gear 114 counter-clockwise, which shortened the length and increased the tension of extension-resisting member 701, which pulled the left side of skeletal member 101 forward and downward (with compression-resisting artificial disc 401 acting as a fulcrum) causing skeletal member 101 to rotate clockwise, which is torsion. The ability to remotely and gradually adjust spinal torsion over time can provide new options for relieving back pain and correcting spinal deformities.

Figure 9:
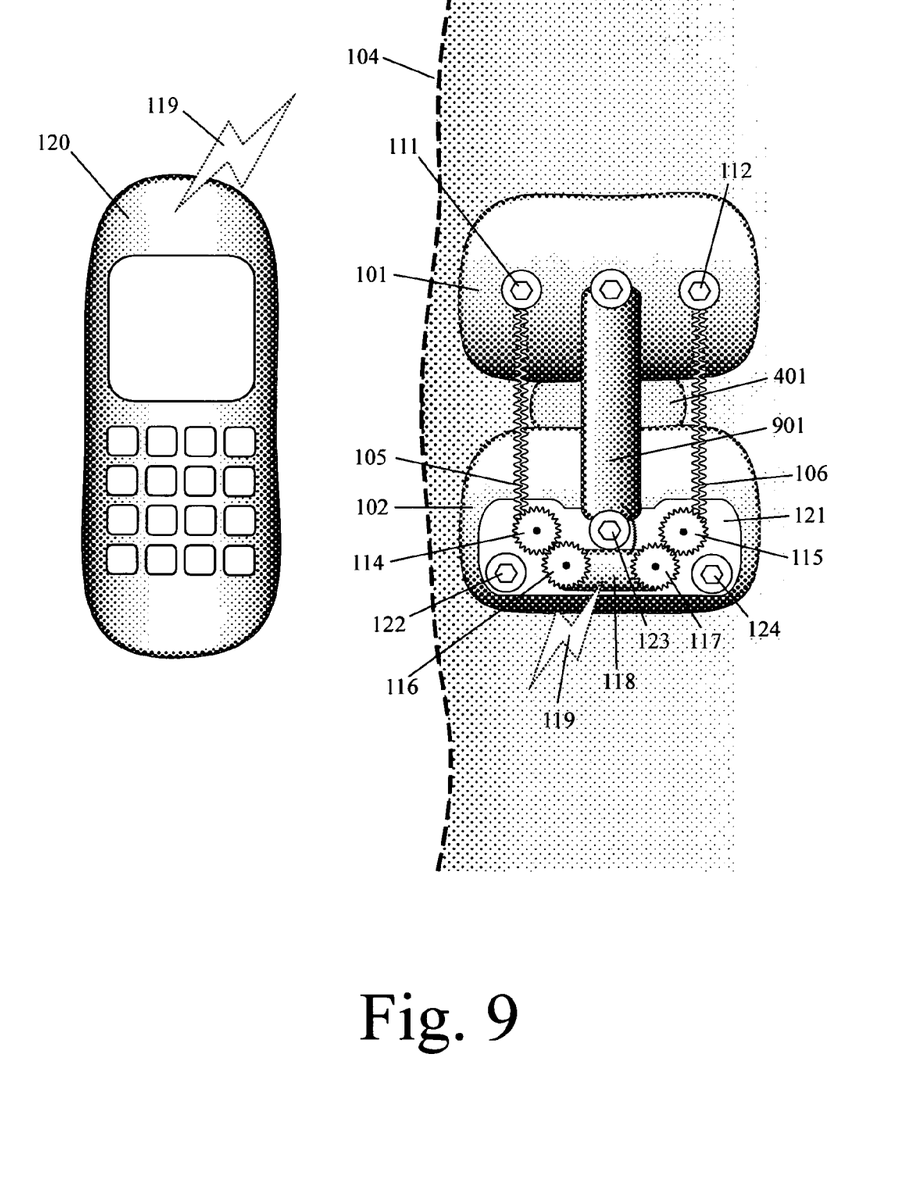
FIG. 9 shows how a sensor may be added to this invention to create a real-time feedback system for making adjustments.

FIG. 9 shows the same example of the invention that is shown in FIG. 4, except that now sensor 901 has been added to provide information that can be used for adjusting the extension-resisting members. In this example, sensor 901 is an electrogoniometer that measures the angle of skeletal member 101 relative to skeletal member 102. In an example, if information from this sensor indicates that the range of motion for the two members is too wide, then the device could automatically shorten the length and increase the tension on both extension-resisting members to reduce the range of motion. If information from this sensor indicates that the range of motion for the two members is too narrow, then the device could automatically lengthen and decrease the tension on both extension-resisting members to increase the range of motion. In other examples, the sensor could collect information concerning other parameters of spinal function or body activity that may be used to make real-time adjustments to spinal range of motion via the device. In different examples, these adjustments may be done manually by a human who evaluates the information, may be done automatically by a smart device, or may be done by a combination of manual and automatic means.

I claim:

1. An implantable device and system that allows post-operative adjustment of the movement, positions, or both movement and positions of members of the skeletal system relative to each other, comprising:
    a first extension-resisting member: wherein this extension-resisting member is implanted into the body of a mammal; wherein this extension-resisting member can be extended by application of force, but which offers resistance to such extension; wherein one or more post-operative changes in the extension-resisting member can be made in a non-invasive or minimally-invasive manner by a human operator, by automatic means, or by both human operator and automatic means, and wherein a change in the extension-resisting member is selected from the group consisting of a change in tension, a change in length, a change in width, and a change in torsion; wherein this extension-resisting member is configured to be connected, directly or indirectly, to two or more members of the skeletal system; and wherein one or more changes in the extension-resisting member can cause one or more movements of the members of the skeletal system relative to each other;
    a second extension-resisting member: wherein this extension-resisting member is implanted into the body of a mammal; wherein this extension-resisting member can be extended by application of force, but which offers resistance to such extension; wherein one or more post-operative changes in the extension-resisting member can be made in a non-invasive or minimally-invasive manner by a human operator, by automatic means, or by both human operator and automatic means, and wherein a change in the extension-resisting member is selected from the group consisting of a change in tension, a change in length, a change in width, and a change in torsion; wherein this extension-resisting member is configured to be connected, directly or indirectly, to two or more members of the skeletal system; and wherein one or more changes in the extension-resisting member can cause one or more movements of the members of the skeletal system relative to each other;
    a compression-resisting member: wherein this compression-resisting member is implanted into the body of a mammal; wherein this compression-resisting member offers resistance to compression; and wherein this compression-resisting member is configured to be connected, directly or indirectly, to two or more members of the skeletal system; and
    an internal control unit; wherein this internal control unit includes an actuator; wherein this internal control unit is implanted into the body of a mammal; wherein this internal control unit enables post-operative changes in an extension-resisting member in a non-invasive or minimally-invasive manner; wherein these changes are selected from the group consisting of a change in tension, a change in length, a change in width, and a change in torsion; and wherein these changes can be adjusted and reversed in a non-invasive or minimally-invasive manner.

2. The extension-resisting members in claim 1 wherein changes in the tension of one or both extension-resisting members cause one or more movements of two or more members of the skeletal system relative to each other.

3. The extension-resisting members in claim 1 wherein changes in the length or width of one or both extension-resisting members cause one or more movements of two or more members of the skeletal system relative to each other.

4. The extension-resisting members in claim 1 wherein these extension-resisting members are selected from the group consisting of: one or more spring-like members; one or more longitudinal members with helical or lateral cuts or slits; one or more extendable fibers; one or more extendable threads; one or more extendable cords; one or more extendable bands; one or more extendable wires; one or more extendable cables; one or more stretchable rods; and one or more extendable members filled with a gas, fluid, or gel.

5. The extension-resisting members in claim 1 wherein the means of post-operative changes in these extension-resisting members is selected from the group consisting of: adjustment by a human operator; automatic adjustment by a control unit; and a combination of human and automatic control.

6. The extension-resisting members in claim 1 wherein post-operative changes in these extension-resisting members are at least partially based on information from a sensor.

7. The compression-resisting member in claim 1 wherein this compression-resisting member is selected from the group consisting of: a longitudinal sequence of compression-resisting segments that are connected in such a way that they can be flexed, tilted, bent, rotated, or a combination of these movements, relative to each other, but resist longitudinal compression when aligned in a straight configuration; a single compression-resisting structure; and an artificial intervertebral disc.

8. The implantable device and system in claim 1 wherein this device and system enables ongoing adjustments of the relative movement, positions, or both movement and positions of members of the skeletal system over time and wherein these ongoing adjustments provide different variations of skeletal movement, flexibility, and/or range of motion to match different activities in which the patient engages at different times.

9. The ongoing adjustments in claim 8 wherein these adjustments help to improve the patient's performance during different activities, help to reduce pain, and/or help to avoid injury.

10. The implantable device and system in claim 1 wherein this device and system is used: to provide dynamic stabilization of the spine; to correct spinal deformity.

11. An implantable device and system that allows post-operative adjustment of the movement, positions, or both movement and positions of members of the skeletal system relative to each other, comprising:
   one or more extension-resisting members: wherein this extension-resisting member is implanted into the body of a mammal; wherein this extension-resisting member can be extended by application of force, but which offers resistance to such extension; wherein one or more post-operative changes in the extension-resisting member can be made in a non-invasive or minimally-invasive manner by a human operator, by automatic means, or by both human operator and automatic means, and wherein a change in the extension-resisting member is selected from the group consisting of a change in tension, a change in length, a change in width, and a change in torsion; wherein this extension-resisting member is configured to be connected, directly or indirectly, to two or more members of the skeletal system; and wherein one or more changes in the extension-resisting member can cause one or more movements of the members of the skeletal system relative to each;
   a compression-resisting member: wherein this compression-resisting member is implanted into the body of a mammal; wherein this compression-resisting member offers resistance to compression; and wherein this compression-resisting member is configured to be connected, directly or indirectly, to two or more members of the skeletal system; and
   an internal control unit; wherein this internal control unit includes an actuator; wherein this internal control unit is implanted into the body of a mammal; wherein this internal control unit enables post-operative changes in an extension-resisting member in a non-invasive or minimally-invasive manner; wherein these changes are selected from the group consisting of a change in tension, a change in length, a change in width, and a change in torsion; and wherein these changes can be adjusted and reversed in a non-invasive or minimally-invasive manner.

12. The extension-resisting members in claim 11 wherein changes in the tension of one or both extension-resisting members cause one or more movements of two or more members of the skeletal system relative to each other.

13. The extension-resisting members in claim 11 wherein changes in the length or width of one or both extension-resisting members cause one or more movements of two or more members of the skeletal system relative to each other.

14. The extension-resisting members in claim 11 wherein the means of post-operative changes in these extension-resisting members is selected from the group consisting of: adjustment by a human operator; automatic adjustment by a control unit; and a combination of human and automatic control.

15. The extension-resisting members in claim 11 wherein post-operative changes in these extension-resisting members are at least partially based on information from a sensor.

16. The implantable device and system in claim 11 wherein this device and system enables ongoing adjustments of the relative movement, positions, or both movement and positions of members of the skeletal system over time and wherein these ongoing adjustments provide different variations of skeletal movement, flexibility, and/or range of motion to match different activities in which the patient engages at different times.

17. The ongoing adjustments in claim 16 wherein these adjustments help to improve the patient's performance during different activities, help to reduce pain, and/or help to avoid injury.

18. The implantable device and system in claim 11 wherein this device and system is used: to provide dynamic stabilization of the spine; to correct spinal deformity.

19. An implantable device and system that allows post-operative adjustment of the movement, positions, or both movement and positions of members of the skeletal system relative to each other, comprising:
   one or more extension-resisting members: wherein this extension-resisting member is implanted into the body of a mammal; wherein this extension-resisting member can be extended by application of force, but which offers resistance to such extension; wherein one or more post-operative changes in the extension-resisting member can be made in a non-invasive or minimally-invasive manner by a human operator, by automatic means, or by both human operator and automatic means, and wherein a change in the extension-resisting member is selected from the group consisting of a change in tension, a change in length, a change in width, and a change in torsion; wherein this extension-resisting member is configured to be connected, directly or indirectly, to two or more members of the skeletal system; and wherein one or more changes in the extension-resisting member can cause one or more movements of the members of the skeletal system relative to each;
   an internal control unit; wherein this internal control unit includes an actuator; wherein this internal control unit is implanted into the body of a mammal; wherein this internal control unit enables post-operative changes in an extension-resisting member in a non-invasive or minimally-invasive manner; wherein these changes are selected from the group consisting of a change in tension, a change in length, a change in width, and a change in torsion; and wherein these changes can be adjusted and reversed in a non-invasive or minimally-invasive manner; and
   a remote control unit; wherein this remote control unit is external to the body and can wirelessly control the internal control unit in a non-invasive or minimally-invasive manner.

* * * * *